United States Patent
Bhat (10) Patent No.: US 10,111,873 B1
(45) Date of Patent: Oct. 30, 2018

(54) DIHYDROPYRIMIDINONE DERIVATIVES

(71) Applicant: KING SAUD UNIVERSITY, Riyadh (SA)

(72) Inventor: Mashooq Ahmad Bhat, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/873,450

(22) Filed: Jan. 17, 2018

(51) Int. Cl.
| | |
|---|---|
| *C07D 413/00* | (2006.01) |
| *A61K 31/513* | (2006.01) |
| *A61K 31/5375* | (2006.01) |
| *A61K 31/12* | (2006.01) |
| *A61K 31/04* | (2006.01) |
| *A61K 31/497* | (2006.01) |

(52) U.S. Cl.
CPC ............ *A61K 31/513* (2013.01); *A61K 31/04* (2013.01); *A61K 31/12* (2013.01); *A61K 31/497* (2013.01); *A61K 31/5375* (2013.01)

(58) Field of Classification Search
CPC .......................... C07D 403/04; C07D 413/04
USPC .................................................. 544/123, 295
See application file for complete search history.

(56) References Cited

U.S. PATENT DOCUMENTS

| | | |
|---|---|---|
| 3,989,701 A | 11/1976 | Toth et al. |
| 4,656,267 A | 4/1987 | Bandurco et al. |
| 7,687,510 B2 | 3/2010 | Gielen-Haertwig et al. |
| 8,039,486 B2 | 10/2011 | Yeung et al. |
| 8,440,663 B2 | 5/2013 | Mann et al. |
| 9,115,093 B2 | 8/2015 | Gnamm et al. |
| 9,119,856 B1 | 9/2015 | Al-Dhfyan et al. |
| 9,440,930 B2 | 9/2016 | Oost et al. |
| 9,458,113 B2 | 10/2016 | Peters et al. |
| 9,856,232 B1 | 1/2018 | Bhat et al. |
| 2010/0121048 A1 | 5/2010 | Kuroita et al. |
| 2012/0189539 A1 | 7/2012 | Wang et al. |
| 2012/0202794 A1 | 8/2012 | Sofia et al. |
| 2014/0248355 A1 | 9/2014 | Bang-Andersen et al. |
| 2014/0329831 A1 | 11/2014 | Li et al. |

FOREIGN PATENT DOCUMENTS

| | | |
|---|---|---|
| JP | 2013177318 A | 9/2013 |
| WO | 90/06118 A1 | 6/1990 |

OTHER PUBLICATIONS

Khabazzadeh et al., "An efficient synthesis of 3,4-dihydropyrimidin-2(1H)-ones catalyzed by molten [Et3NH][HSO4]," Arabian Journal of Chemistry, vol. 5(10), pp. 485-488, Available online Sep. 12, 2010.
Lukas, R. J. et. al., Synthesis and Characterization of in Vitro and in Vivo Profiles of Hydroxybupropion Analogues: Aids to Smoking Cessation J. Med. Chem., 2010; 53: 4731.
Sabine, Kuettel. et. al., Synthesis and Evaluation of Antiparasitic Activities of New 4-[5-(4-Phenoxyphenyl)-2H-pyrazol-3-yl]morpholine Derivatives, J. Med. Chem.; 2007; 50; 5833-5839.
Jeffrey, J. Hale. et. al., Phosphorylated Morpholine Acetal Human Neurokinin-1 Receptor Antagonists as Water-Soluble Prodrugs, J. Med. Chem. 2000; 43; 1234-1241.
Michael, C. Chrysselis. et. al., Hypocholesterolemic and Hypolipidemic Activity of Some Novel Morpholine Derivatives with Antioxidant Activity, J. Med. Chem.; 2000; 43; 609-612.

*Primary Examiner* — Jeffrey H Murray
(74) *Attorney, Agent, or Firm* — Richard C. Litman (57) ABSTRACT

A dihydropyrimidinone derivative having a chemical structure according to Formula 1:

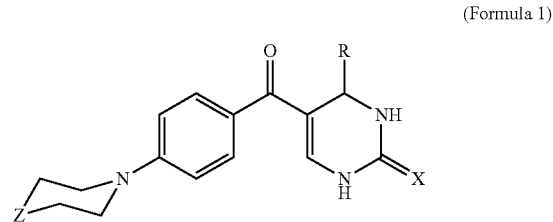

(Formula 1)

wherein
Z is selected from N and O;
X is selected from O and S; and
R represents aryl, substituted aryl, heteroaryl, or substituted heteroaryl, wherein the substituted aryl or substituted heteroaryl have one or more substituents selected from halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

14 Claims, 2 Drawing Sheets

DIHYDROPYRIMIDINONE DERIVATIVES

BACKGROUND

1. Field

The disclosure of the present patent application relates generally to piperazine/morpholine linked dihydropyrimidinone derivatives, and methods for preparing these derivatives. In particular, the application focuses on 4-(substituted phenyl)-5-[4-(piperazin/morpholin-1-yl)benzoyl]-3,4-dihydropyrimidin-2(1H)-one derivatives and methods for their preparation.

2. Description of the Related Art

Piperazine consists of six membered heterocyclic rings containing two nitrogen atoms at two opposite positions. Piperazine moiety containing polar nitrogen atoms confers bioactivity to the molecule and increases favorable interactions with macromolecules. Piperazine has the ability to cross the blood brain barrier (BBB) due to its small size and lipophilic nature which promote its activity upon central nervous system (CNS) diseases which include anxiety disorders, Alzheimer's disease, psychosis and depression. Many potent marketed drugs like flunarizine, cinnarizine, lomerizine, fluphenazine, ciprofloxacin, Merck HIV protease, and crixivan, have a piperazine moiety. Piperazine derivatives have been found to be potent agents in the treatment of various ailments, such as CNS agents, anticancer, cardio-protective agents, antiviral, anti-tuberculosis, anti-inflammatory, anti-diabetic, and antihistamine profiles, as well as agents for relieving pain and for use in imaging applications.

Morpholine is an organic moiety containing nitrogen and oxygen in a heterocyclic six membered ring and is considered an important building block in the field of medicinal chemistry. The Linezolid antibiotic having a morpholine moiety is commercially available as an antimicrobial agent. A selective inhibitor of epidermal growth factor Timolol (non-selective beta-adrenergic receptor antagonist indicated for treating glaucoma) Moclobemide, Emorfazone (anti-inflammatory drug and analgesic), Phenadoxone (Heptalgin, opioid analgesic), anti-depressants Reboxetine and Gefitinib, appetite suppressants Phenmetrazine (Preludin, 3-methyl-2-phenylmorpholine) and 2-benzylmorpholine and Canertinib, Fenpropimorph (fungicide), and antibacterial drugs Finafloxacin, Levofloxacin. Morpholine derivatives are very essential in the drug discovery process. The morpholine scaffold is important due to its variety of pharmacological activities, including analgesic, anti-inflammatory, anticancer, antidepressant, HIV-protease inhibitors, appetite suppressant, local anaesthetic, antiplatelet, selective inhibitor of protein kinase C, antitumor, neuroprotective, antifungal, anti-tuberculosis, anti-parasitic, anti-malarial, hypolipidemic and hypocholesterolemic activities.

Pyrimidines have played an important role in medicinal chemistry. Pyrimidines are important scaffolds in the field of medicinal chemistry because of their potential biological activities, including use as anti-tumor, anti-virus and anti-bacterial agents. Some pyrimidines have been used as potential anti-hypertensive agents. 4-Aryl-1,4-dihydropyridines, like Nifedipine, were first introduced as antihypertensive agents used in medicine in 1975. Dihydropyridines are the most potent calcium channel modulators available for the treatment of various cardiovascular diseases.

Substituted dihydropyrimidinone compounds have been shown to possess interesting biological properties. Some of the analogs of dihydropyrimidine compounds are antitumor agents. Dihydropyrimidinones have emerged as the integral back bone of calcium channel blockers, or antihypertensive agents. Some of these compounds have exhibited a broad range of other biological activities such as antiviral, antitumor, antibacterial and anti-inflammatory.

Dihydropyrimidinone compounds were first synthesized by Pietro Beginelli. The compounds were known as Biginelli compounds. The compounds were produced by reacting aldehydes with urea and a beta-keto ester, producing a tetrahydropyrimidinone.

Since Biginelli's time, a number of procedures have been described for synthesizing dihydropyrimidinone compounds and their derivatives. However, in view of the established medical and pharmaceutical value of this family of compounds, there is still a need for new dihydropyrimidinone compounds and synthesis procedures.

Thus, dihydropyrimidinone derivatives solving the aforementioned problems is desired.

SUMMARY

The dihydropyrimidinone derivatives include 4-(substituted phenyl)-5-[4-(piperazin/morpholin-1-yl)benzoyl]-3,4-dihydro-pyrimidin-2(1H)-one derivatives having a chemical structure according to Formula 1:

(Formula 1)

wherein
- Z is selected from N and O;
- X is selected from O and S; and
- R represents aryl, substituted aryl, heteroaryl, or substituted heteroaryl, wherein the substituted aryl or substituted heteroaryl have one or more substituents selected from halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

An embodiment of the present subject matter is directed to a method of making a dihydropyrimidinone derivative, including refluxing 1-[4-(piperazin/morpholin-1-yl) phenyl] ethan-1-one (0.01 mol) with dimethylformamide dimethylacetal (DMF-DMA) (0.013 mol) to obtain enaminone; and refluxing a solution of enaminone (0.01 mol), substituted benzaldehyde (0.01 mol), and urea (0.01 mol) to yield dihydropyrimidinone derivatives having a structure of:

(Formula 1)

wherein
- Z is selected from N and O;
- X is selected from O and S; and
- R represents an aryl, substituted aryl, heteroaryl, or substituted heteroaryl, wherein the substituted aryl or substituted heteroaryl have one or more substituents selected from the group consisting of halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

Another embodiment of the present subject matter is directed to the dihydropyrimidinone derivative described above or a method of preparing the derivative, where R is substituted aryl or substituted heteroaryl with one or more substituents selected from halogen, alkyl, haloalkyl, alkoxy, haloalkoxy, nitro, hydroxyl, alkylthio, alkylamino, heteroaryl, aryloxy, haloaryloxy, arylthio, and arylamino.

Another embodiment is directed to the dihydropyrimidinone derivative described above or a method of preparing the derivative, where R is phenyl, 2-nitrophenyl, 3-nitrophenyl, 4-nitrophenyl, 4-chlorophenyl, 2-methoxyphenyl, 4-hydroxyphenyl, 3-hydroxyphenyl, 3-methoxyphenyl, or 4-ethoxy phenyl.

Another embodiment is directed to the dihydropyrimidinone derivative described above or a method of preparing the derivative, where the derivative has the chemical structure of any of DHPM-1 to DHPM-20 as defined and depicted herein.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A dihydropyrimidinone derivative includes a compound having a chemical structure according to Formula 1, shown below:

(Formula 1)

wherein

Z is selected from N and O;

X is selected from O and S; and

R represents aryl, substituted aryl, heteroaryl, or substituted heteroaryl, wherein the substituted aryl or substituted heteroaryl have one or more substituents selected from halogen, alkyl, haloalkyl, alkoxy, haloalkoxy, nitro, hydroxyl, alkylthio, alkylamino, heteroaryl, aryloxy, haloaryloxy, arylthio, arylamino, and pharmaceutically acceptable salts thereof.

In an embodiment, R represents mono-substituted phenyl compounds. In an embodiment, R is selected from phenyl, 2-nitrophenyl, 3-nitrophenyl, 4-nitrophenyl, 4-chlorophenyl, 2-methoxyphenyl, 4-hydroxyphenyl, 3-hydroxyphenyl, 3-methoxyphenyl, 4-ethoxy phenyl.

The dihydropyrimidinone derivatives can include 4-(substituted phenyl)-5-[4-(piperazin/morpholin-1-yl)benzoyl]-3,4-dihydropyrimidin-2(1H)-one derivatives. In an embodiment of the present subject matter, the dihydropyrimidinone derivatives include one or more of compounds DHPM 1-20 provided below:

(DHPM-1)

(DHPM-2)

(DHPM-3)

(DHPM-4)

(DHPM-5)

(DHPM-6)

(DHPM-7)

(DHPM-8)

(DHPM-9)

(DHPM-10)

(DHPM-11)

(DHPM-12)

(DHPM-13)

(DHPM-14)

(DHPM-15)

(DHPM-16)

(DHPM-17)

(DHPM-18)

(DHPM-19)

(DHPM-20)

Figure 1:
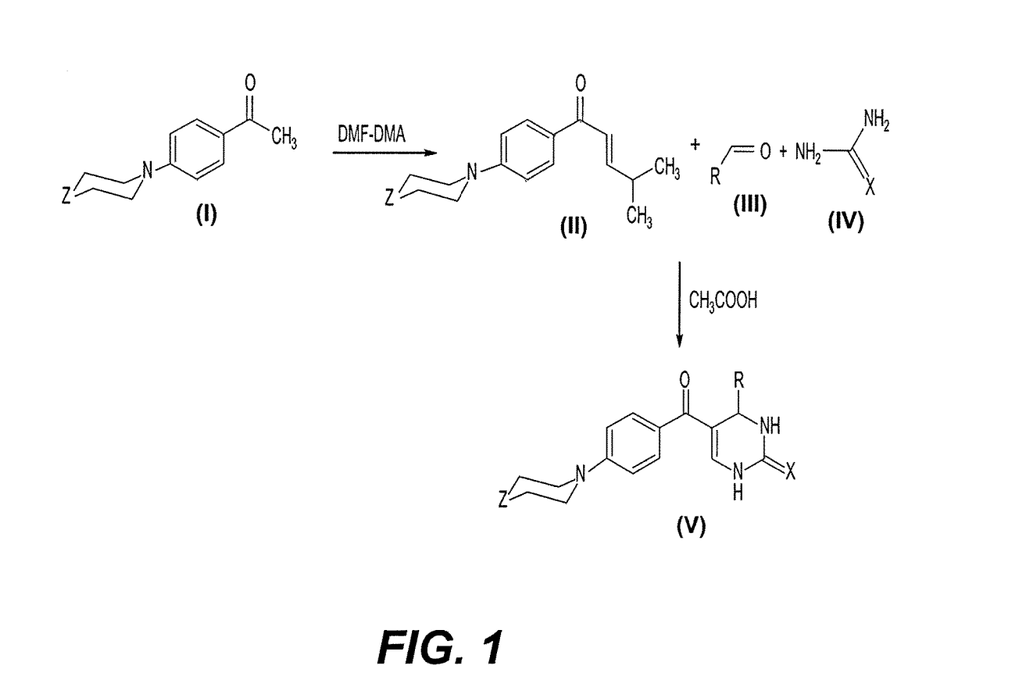
FIG. 1 illustrates the reaction scheme by which the dihydropyrimidinone derivatives can be prepared.

FIG. 1 depicts a reaction scheme by which the dihydropyrimidinone derivatives of Formula 1 can be prepared. As shown in FIG. 1, the dihydropyrimidinone derivatives can be synthesized by refluxing 1-[4-(piperazin/morpholin-1-yl) phenyl]ethan-1-one (I) with dimethylformamide dimethylacetal (DMF-DMA) to obtain the enaminone (II); and refluxing a solution of the enaminone (II), a substituted benzaldehyde (III), urea (IV), and glacial acetic acid to yield the dihydropyrimidinone derivative (V) of Formula 1, where X, Z, and R represent the moieties recited above.

In one embodiment, the 1-[4-(piperazin/morpholin-1-yl) phenyl]ethan-1-one is refluxed with dimethylformamide dimethylacetal (DMF-DMA) under a solvent free condition for about 10 hours.

In another embodiment, the solution of enaminone, substituted benzaldehyde, urea, and glacial acetic acid is refluxed for about 3 hours.

In another embodiment, the method further includes recrystallizing the 4-(substituted phenyl)-5-[4-(piperazin/morpholin-1-yl)benzoyl]-3,4-dihydropyrimidin-2(1H)-one derivatives from the ethanol and glacial acetic acid mixture.

It is anticipated that the compounds described herein can provide a one or more therapeutic uses, including, for example, anti-tumor, anti-viral, anti-bacterial, anti-inflammatory, anti-cancer, cardio-protective, anti-tuberculosis, anti-diabetic, antihistamine, antidepressant, inhibiting HIV-protease, antiplatelet, inhibitor of protein kinase C, neuroprotective, anti-hypertensive, anti-fungal, anti-parasitic, anti-malarial, hypolipidemic, hypocholesterolemic, treatment of chronic wounds, treatment of Hunner's ulcer, treatment of ulcerative colitis, and/or inhibiting neutrophil elastase activity. For example, the dihydropyrimidinone derivatives can be used as an active ingredient in a pharmaceutical composition for treatment of one or more ailments. The pharmaceutical composition can include one or more of the dihydropyrimidinone derivatives, or salt thereof, and a pharmaceutical carrier. The pharmaceutical composition including the one or more dihydropyrimidinone derivatives can be prepared and administered in any suitable manner, such as that described in U.S. Pat. No. 9,856,232, issued Jan. 2, 2018 to Bhat et al., which is hereby incorporated by reference in its entirety The following example illustrates the present teachings.

EXAMPLE

Synthesis of the Dihydropyrimidinone Derivatives

As shown in FIG. 1, enaminone (II), (2E)-4-methyl-1-[4-(piperazin/morpholin-1-yl)phenyl]pent-2-en-1-one was synthesized by refluxing 1-[4-(piperazin/morpholin-1-yl) phenyl]ethan-1-one (I) with dimethylformamide dimethylacetal (DMF-DMA) under solvent-free conditions for 10 hours. A single crystal X-ray structure confirmed the three dimensional structure of enaminone (II). The CCDC number 1532829 contains the crystallographic data for the enaminone structure (II) having the morpholine moiety—where the substituent Z is oxygen.

Figure 2A:
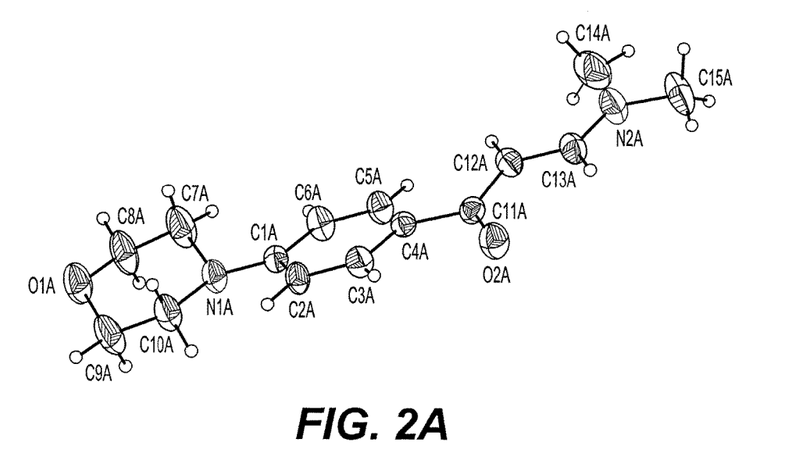
FIG. 2A and FIG. 2B illustrate two conformers in the unit cell of the crystal X-ray structure of enaminone II (as labeled in FIG. 1).
Figure 2B:
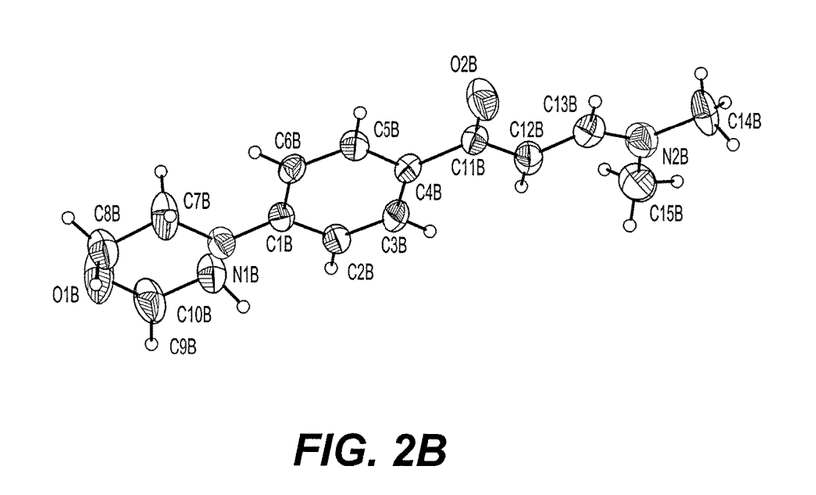

To prepare the final dihydropyrimidinone derivatives, a solution of the enaminone (II) (0.01 mol), the substituted benzaldehyde (0.01 mol) III, urea (0.01 mol) IV, and glacial acetic acid (10 mL) was heated under reflux for 3 hours. The precipitate of the resulting corresponding compounds DHPM 1-20 were collected by filtration, washed with water and recrystallized from a mixture of glacial acetic acid and ethanol. In the spectra produced when analyzed by NMR spectroscopy, the signals of the individual protons of the compounds were verified on the basis of multiplicity, chemical shifts and the coupling constant. FIG. 2A and FIG. 2B illustrate two conformers in the unit cell of the crystal X-ray structure of enaminone II Analytical and spectral data for the compounds were confirmed in comparison with the expected structures of the compounds.

The spectral data for compounds DHPM 1-20 are provided below:

DHPM-1 4-phenyl-5-[4- (piperazin-1-yl)benzoyl]-3,4-dihydropyrimidin-2(1H)-one Yield: 75%; m.p.: 150-152° C.; $^1$H NMR (500 MHz, DMSO-d$_6$): δ=9.41 (1H, s, NH, D$_2$O exchg.), 8.50 (1H, s, NH, D$_2$O exchg.), 8.0 (1H, s, =CH), 6.90-7.80 (9H, m, Ar—H), 6.0 (1H, s, H-4), 3.40 (2H, s, CH$_2$ piperazine), 3.31 (2H, s, CH$_2$ piperazine), 2.06 (2H, s, CH$_2$ piperazine), 2.0 (2H, s, CH$_2$ piperazine), 1.80 (1H, s, NH, D$_2$O exchg.); MS: m/z=362.42 [M]$^+$; Analysis: for C$_{21}$H$_{22}$N$_4$O$_2$, calcd. C 69.59, H 6.12, N 15.46%; found C 69.32, H 6.10, N 15.40%.

DHPM-2 4-(2-Nitrophenyl)-5-[4-(piperazin-1-yl)benzoyl]-3,4-dihydropyrimidin-2(1H)-one Yield: 70%; m.p.: 170-172° C.; $^1$H NMR (500 MHz, DMSO-d$_6$): δ=9.4 (1H, s, NH, D$_2$O exchg.), 8.52 (1H, s, NH, D$_2$O exchg.), 8.04 (1H, s, =CH), 6.89-7.88 (8H, m, Ar—H), 6.07 (1H, s, H-4), 3.41 (2H, s, CH$_2$ piperazine), 3.32 (2H, s, CH$_2$ piperazine), 2.06 (2H, s, CH$_2$ piperazine), 2.0 (2H, s, CH$_2$ piperazine), 1.79 (1H, s, NH, D$_2$O exchg.); $^{13}$C NMR (125.76 MHz, DMSO-d$_6$): δ=44.7, 47.2, 48.4, 50.11, 65.4, 111.7, 113.6, 114.1, 114.5, 124.4, 130.5, 134.1, 138.7, 148.3, 149.1, 151.2, 161.5, 168.9, 190.40, 207.0; MS: m/z=407.40 [M]$^+$; Analysis: for C$_{21}$H$_{21}$N$_5$O$_4$, calcd. C 61.91, H 5.20, N 17.19%; found C 62.15, H 5.22, N 17.12%.

DHPM-3 4-(4-Nitrophenyl)-5-[4-(piperazin-1-yl)benzoyl]-3,4-dihydropyrimidin-2(1H)-one Yield: 75%; m.p.: 175-177° C.; $^1$H NMR (500 MHz, DMSO-d$_6$): δ=9.41 (1H, s, NH, D$_2$O exchg.), 8.28 (1H, s, =CH), 6.93-7.58 (8H, m, Ar—H), 7.93 (1H, s, NH, D$_2$O exchg.), 5.55 (1H, s, H-4), 3.30 (2H, s, CH$_2$ piperazine), 3.23 (2H, s, CH$_2$ piperazine), 2.07 (2H, s, CH$_2$ piperazine), 2.0 (2H, s, CH$_2$ piperazine), 1.85 (1H, s, NH, D$_2$O exchg.); $^{13}$C NMR (125.76 MHz, DMSO-d$_6$): δ=44.7, 45.5, 47.2, 47.5, 48.0, 53.9, 118.8, 114.1, 124.3, 128.3, 130.6, 147.2, 151.6, 153.1, 161.3, 168.8, 190.4, 207.0; MS: m/z=407.42 [M]$^+$; Analysis: for C$_{21}$H$_{21}$N$_5$O$_4$, calcd. C 61.91, H 5.20, N 17.19%; found C 62.10, H 5.23, N 17.13%.

DHPM-4 4-(3-Nitrophenyl)-5-[4-(piperazin-1-yl)benzoyl]-3,4-dihydropyrimidin-2(1H)-one Yield: 75%; m.p.: 180-182° C.; $^1$H NMR (500 MHz, DMSO-d$_6$): δ=9.42 (1H, s, NH, D$_2$O exchg.), 8.23 (1H, s, =CH), 6.93-7.65 (8H, m, Ar—H), 7.95 (1H, s, NH, D$_2$O exchg.), 5.58 (1H, s, H-4), 3.31 (2H, s, CH$_2$ piperazine), 3.23 (2H, s, CH$_2$ piperazine), 2.07 (2H, s, CH$_2$ piperazine), 2.01 (2H, s, CH$_2$ piperazine), 1.87 (1H, s, NH, D$_2$O exchg.); $^{13}$C NMR (125.76 MHz, DMSO-d$_6$): δ=44.7, 45.5, 47.2, 47.5, 48.0, 48.4, 53.8, 65.4, 111.8, 114.1, 121.6, 122.9, 128.3, 130.3, 131.3, 133.7, 146.7, 148.2, 151.6, 161.3, 168.8, 190.5, 207.0; MS: m/z=407.42 [M]$^+$; Analysis: for C$_{21}$H$_{21}$N$_5$O$_4$, calcd. C 61.91, H 5.20, N 17.19%; found C 60.67, H 5.22, N 17.10%.

DHPM-5 4-(4-Chlorophenyl)-5-[4-(piperazin-1-yl)benzoyl]-3,4-dihydropyrimidin-2(1H)-one Yield: 75%; m.p.: 160-162° C.; $^1$H NMR (500 MHz, DMSO-d$_6$): δ=9.32 (1H, s, NH, D$_2$O exchg.), 8.50 (1H, s, NH, D$_2$O exchg.), 8.23 (1H, s, =CH), 6.95-8.11 (8H, m, Ar—H), 5.46 (1H, s, H-4), 3.31 (2H, s, CH$_2$ piperazine), 3.23 (2H, s, CH$_2$ piperazine), 2.09 (2H, s, CH$_2$ piperazine), 2.04 (2H, s, CH$_2$ piperazine), 1.90 (1H, s, NH, D$_2$O exchg.); $^{13}$C NMR (125.76 MHz, DMSO-d$_6$): δ=44.7, 44.9, 47.3, 48.0, 48.4, 53.6, 65.4, 112.5, 114.1, 115.6, 116.0, 128.5, 140.0, 143.6, 148.1, 151.8, 153.1, 156.7, 161.3, 168.7, 190.5, 207.0; MS: m/z=396.87 [M]$^+$; Analysis: for C$_{21}$H$_{21}$ClN$_4$O$_2$, calcd. C 63.55, H 5.33, N 14.12%; found C 63.31, H 5.34, N 14.17%.

DHPM-6 4-(2-methoxyphenyl)-5-[4-(piperazin-1-yl)benzoyl]-3,4-dihydropyrimidin-2(1H)-one Yield: 75%; m.p.: 120-122° C.; $^1$H NMR (500 MHz, DMSO-d$_6$): δ=9.22 (1H, s, NH, D$_2$O exchg.), 8.51 (1H, s, NH, D$_2$O exchg.), 8.13 (1H, s, =CH), 6.93-7.98 (8H, m, Ar—H), 5.77 (1H, s, H-4), 3.82 (3H, s, OCH$_3$), 3.41 (2H, s, CH$_2$ piperazine), 3.24 (2H, s, CH$_2$ piperazine), 2.09 (2H, s, CH$_2$ piperazine), 2.04 (2H, s, CH$_2$ piperazine), 1.93 (1H, s, NH, D$_2$O exchg.); $^{13}$C NMR (125.76 MHz, DMSO-d$_6$): δ=44.6, 46.7, 48.0, 48.5, 49.6, 55.9, 56.1, 111.1, 112.1, 114.2, 120.6, 121.1, 130.5, 131.0, 137.3, 154.0, 157.3, 158.5, 161.4, 168.8, 172.6, 187.1, 190.5, 196.1, 207.0; MS: m/z=392.45 [M]$^+$; Analysis: for C$_{22}$H$_{24}$N$_4$O$_3$, calcd. C 67.33, H 6.16, N 14.28%; found C 67.58, H 6.14, N 14.23%.

DHPM-7 4-(4-Hydroxyphenyl)-5-[4-(piperazin-1-yl)benzoyl]-3,4-dihydropyrimidin-2(1H)-one Yield: 75%; m.p.: 210-212° C.; $^1$H NMR (500 MHz, DMSO-d$_6$): δ=9.16 (1H, s, OH, D$_2$O exchg.), 9.0 (1H, s, NH, D$_2$O exchg.), 8.51 (1H, s, NH, D$_2$O exchg.), 8.17 (1H, s, =CH), 6.71-8.08 (8H, m, Ar—H), 5.33 (1H, s, H-4), 3.35 (2H, s, CH$_2$ piperazine), 3.20 (2H, s, CH$_2$ piperazine), 2.07 (2H, s, CH$_2$ piperazine), 2.01 (2H, s, CH$_2$ piperazine), 1.82 (1H, s, NH, D$_2$O exchg.); $^{13}$C NMR (125.76 MHz, DMSO-d$_6$): δ=44.7, 47.3, 48.1, 49.2, 53.5, 65.4, 115.4, 116.0, 128.0, 129.6, 130.3, 151.7, 152.0, 153.0, 155.8, 156.4, 157.1, 159.1, 161.3, 168.8, 190.7, 207.0; MS: m/z=378.42 [M]$^+$; Analysis: for C$_{21}$H$_{22}$N$_4$O$_3$, calcd. C 66.65, H 5.86, N 14.81%; found C 66.40, H 5.84, N 14.86%.

DHPM-8 4-(3-Hydroxyphenyl)-5-[4-(piperazin-1-yl)benzoyl]-3,4-dihydropyrimidin-2(1H)-one Yield: 75%; m.p.: 158-160° C.; $^1$H NMR (500 MHz, DMSO-d$_6$): δ=9.8 (1H, s, OH, D$_2$O exchg.), 9.10 (1H, s, NH, D$_2$O exchg.), 8.04 (1H, s, =CH), 6.82-7.77 (8H, m, Ar—H), 6.71 (1H, s, NH, $D_2O$ exchg.), 5.32 (1H, s, H-4), 3.30 (2H, s, $CH_2$ piperazine), 3.20 (2H, s, $CH_2$ piperazine), 2.04 (2H, s, $CH_2$ piperazine), 2.0 (2H, s, $CH_2$ piperazine), 1.86 (1H, s, NH, $D_2O$ exchg.); $^{13}C$ NMR (125.76 MHz, DMSO-$d_6$): δ=44.6, 46.7, 47.9, 48.0, 53.8, 56.5, 115.5, 117.3, 120.1, 122.9, 128.6, 130.5, 136.7, 139.5, 143.0, 146.1, 152.1, 153.1, 154.0, 157.8, 161.4, 168.8, 172.6, 187.0, 190.6, 196.6, 207.0; MS: m/z=378.42 [M]$^+$; Analysis: for $C_{21}H_{22}N_4O_3$, calcd. C 66.65, H 5.86, N 14.81%; found C 66.39, H 5.83, N 14.85%.

DHPM-9 4-(3-methoxyphenyl)-5-[4-(piperazin-1-yl)benzoyl]-3,4-dihydropyrimidin-2(1H)-one Yield: 70%; m.p.: 118-120° C.; $^1H$ NMR (500 MHz, DMSO-$d_6$): δ=9.28 (1H, s, NH, $D_2O$ exchg.), 8.50 (1H, s, NH, $D_2O$ exchg.), 8.24 (1H, s, =CH), 6.88-8.11 (8H, m, Ar—H), 5.47 (1H, s, H-4), 3.73 (3H, s, $OCH_3$), 3.33 (2H, s, $CH_2$ piperazine), 3.20 (2H, s, $CH_2$ piperazine), 2.09 (2H, s, $CH_2$ piperazine), 2.04 (2H, s, $CH_2$ piperazine), 1.92 (1H, s, NH, $D_2O$ exchg.); $^{13}C$ NMR (125.76 MHz, DMSO-$d_6$): δ=44.6, 44.7, 46.8, 47.3, 55.4, 65.4, 112.7, 114.1, 118.9, 130.5, 136.8, 139.9, 142.8, 146.1, 151.7, 152.0, 153.1, 154.0, 159.7, 160.1, 161.4, 172.7, 187.0, 190.6, 196.1; MS: m/z=392.45 [M]$^+$; Analysis: for $C_{22}H_{24}N_4O_3$, calcd. C 67.33, H 6.16, N 14.28%; found C 67.57, H 6.14, N 14.23%.

DHPM-10 4-(3-Ethoxyphenyl)-5-[4-(piperazin-1-yl)benzoyl]-3,4-dihydropyrimidin-2(1H)-one Yield: 65%; m.p.: 88-90° C.; $^1H$ NMR (500 MHz, DMSO-$d_6$): δ=9.21 (1H, s, NH, $D_2O$ exchg.), 8.52 (1H, s, NH, $D_2O$ exchg.), 8.20 (1H, s, =CH), 6.87-8.11 (8H, m, Ar—H), 5.40 (1H, s, H-4), 4.0 (2H, q, $OCH_2$), 3.33 (2H, s, $CH_2$ piperazine), 3.20 (2H, s, $CH_2$ piperazine), 2.09 (2H, s, $CH_2$ piperazine), 2.08 (2H, s, $CH_2$ piperazine), 1.92 (1H, s, NH, $D_2O$ exchg.), 1.35 (3H, t, $CH_3$); $^{13}C$ NMR (125.76 MHz, DMSO-$d_6$): δ=15.0, 15.1, 21.5, 21.6, 26.6, 31.1, 44.6, 46.8, 47.3, 48.0, 48.5, 63.7, 114.2, 114.6, 115.1, 128.0, 130.5, 130.9, 131.0, 153.9, 158.2, 160.8, 161.4, 172.5, 186.9, 190.6, 191.7, 196.1; MS: m/z=406.43 [M]$^+$; Analysis: for $C_{23}H_{26}N_4O_3$, calcd. C 67.96, H 6.45, N 13.78%; found C 67.70, H 4.46, N 13.73%.

DHPM-11 5-[4-(morpholin-4-yl)benzoyl]-4-phenyl-3,4-dihydropyrimidin-2(1H)-one Yield: 70%; m.p.: 258-260° C.; $^1H$ NMR (500 MHz, DMSO-$d_6$): δ=9.21 (1H, s, NH, $D_2O$ exchg.), 7.79 (1H, s, =CH), 7.09-7.45 (6H, m, Ar—H), 7.01 (1H, s, NH, $D_2O$ exchg.), 6.95 (3H, m, Ar—H), 5.44 (1H, s, H-4), 3.74 (4H, t, J=4.6 Hz, $2×CH_2$ morpholine), 3.22 (4H, t, J=4.8 Hz, $2×CH_2$ morpholine); $^{13}C$ NMR (125.76 MHz, DMSO-d6): δ=47.6, 54.0, 66.3, 112.9, 113.8, 126.8, 127.8, 128.9, 130.4, 139.8, 144.6, 151.9, 153.3, 153.5, 190.6; MS: m/z=363.42 [M]$^+$; Analysis: for $C_{21}H_{21}N_3O_3$, calcd. C 69.41, H 5.82, N 11.56%; found C 69.58, H 5.80, N 11.59%.

DHPM-12 5-[4-(morpholin-4-yl)benzoyl]-4-(2-nitrophenyl)-3,4-dihydropyrimidin-2(1H)-one Yield: 75%; m.p.: 198-200° C.; $^1H$ NMR (500 MHz, DMSO-$d_6$): δ=9.42 (1H, d, NH, $D_2O$ exchg.), 8.07 (1H, s, =CH), 7.06-7.91 (8H, m, Ar—H), 6.93 (1H, s, NH, $D_2O$ exchg.), 6.08 (1H, s, H-4), 3.73 (4H, t, J=4.6 Hz, $2×CH_2$ morpholine), 3.21 (4H, t, J=4.7 Hz, $2×CH_2$ morpholine); $^{13}C$ NMR (125.76 MHz, DMSO-d6): δ=47.0, 47.6, 50.0, 66.2, 111.7, 113.4, 124.4, 128.1, 129.2, 130.0, 132.6, 134.3, 138.7, 140.8, 148.3, 151.1, 153.5, 190.3, 192.8; MS: m/z=408.43 [M]$^+$; Analysis: for $C_{21}H_{20}N_4O_5$, calcd. C 61.76, H 4.94, N 13.72%; found C 61.90, H 4.92, N 13.77%.

DHPM-13 5-[4-(morpholin-4-yl)benzoyl]-4-(4-nitrophenyl)-3,4-dihydropyrimidin-2(1H)-one Yield: 70%; m.p.: 202-204° C.; $^1H$ NMR (500 MHz, DMSO-$d_6$): δ=9.42 (1H, d, NH, $D_2O$ exchg.), 8.23 (1H, s, =CH), 7.43-7.92 (6H, m, Ar—H), 7.09 (1H, s, NH, $D_2O$ exchg.), 6.94 (2H, d, J=8.9 Hz, Ar—H), 5.57 (1H, s, H-4), 3.72 (4H, t, J=4.6 Hz, $2×CH_2$ morpholine), 3.21 (4H, t, J=4.7 Hz, $2×CH_2$ morpholine); $^{13}C$ NMR (125.76 MHz, DMSO-d6): δ=47.6, 53.9, 66.2, 111.8, 113.8, 124.3, 128.2, 130.5, 140.7, 147.2, 151.7, 153.6, 190.5; MS: m/z=408.42 [M]$^+$; Analysis: for $C_{21}H_{20}N_4O_5$, calcd. C 61.76, H 4.94, N 13.72%; found C 61.90, H 4.92, N 13.76%.

DHPM-14 5-[4-(morpholin-4-yl)benzoyl]-4-(3-nitrophenyl)-3,4-dihydropyrimidin-2(1H)-one Yield: 70%; m.p.: 205-207° C.; $^1H$ NMR (500 MHz, DMSO-$d_6$): δ=9.40 (1H, d, NH, $D_2O$ exchg.), 8.15 (1H, s, =CH), 7.45-7.95 (6H, m, Ar—H), 7.12 (1H, s, NH, $D_2O$ exchg.), 6.95 (2H, d, J=8.9 Hz, Ar—H), 5.59 (1H, s, H-4), 3.72 (4H, t, J=4.6 Hz, $2×CH_2$ morpholine), 3.22 (4H, t, J=4.7 Hz, $2×CH_2$ morpholine); $^{13}C$ NMR (125.76 MHz, DMSO-d6): δ=47.6, 53.7, 66.3, 111.8, 113.8, 121.6, 122.9, 128.2, 130.5, 130.7, 133.7, 140.8, 146.7, 148.2, 151.6, 153.6, 190.5; MS: m/z=408.41 [M]$^+$; Analysis: for $C_{21}H_{20}N_4O_5$, calcd. C 61.76, H 4.94, N 13.72%; found C 61.89, H 4.91, N 13.75%.

DHPM-15 4-(4-chlorophenyl)-5-[4-(morpholin-4-yl)benzoyl]-3,4-dihydropyrimidin-2(1H)-one Yield: 80%; m.p.: 288-290° C.; $^1H$ NMR (500 MHz, DMSO-$d_6$): δ=9.25 (1H, d, NH, $D_2O$ exchg.), 7.81 (1H, s, =CH), 7.33-7.45 (6H, m, Ar—H), 7.02 (1H, s, NH, $D_2O$ exchg.), 6.95 (2H, d, J=8.5 Hz, Ar—H), 5.43 (1H, s, H-4), 3.73 (4H, t, J=4.6 Hz, $2×CH_2$ morpholine), 3.22 (4H, t, J=4.7 Hz, $2×CH_2$ morpholine); $^{13}C$ NMR (125.76 MHz, DMSO-d6): δ=47.6, 53.6, 66.3, 112.5, 113.8, 128.4, 128.8, 128.9, 130.5, 132.3, 140.1, 143.6, 151.8, 153.5, 190.6; MS: m/z=397.86 [M]$^+$; Analysis: for $C_{21}H_{20}ClN_3O_3$, calcd. C 63.40, H 5.07, N 10.56%; found C 63.65, H 5.08, N 10.59%.

DHPM-16 4-(2-methoxyphenyl)-5-[4-(morpholin-4-yl)benzoyl]-3,4-dihydropyrimidin-2(1H)-one Yield: 80%; m.p.: 178-180° C.; $^1H$ NMR (500 MHz, DMSO-$d_6$): δ=9.22 (1H, s, NH, $D_2O$ exchg.), 7.81 (1H, s, =CH), 7.20-7.50 (5H, m, Ar—H), 7.09 (1H, s, NH, $D_2O$ exchg.), 6.89-7.01 (3H, m, Ar—H), 5.75 (1H, s, H-4), 3.82 (4H, t, J=4.7 Hz, $2×CH_2$ morpholine), 3.21 (4H, t, J=4.7 Hz, $2×CH_2$ morpholine); $^{13}C$ NMR (125.76 MHz, DMSO-d6): δ=47.6, 49.6, 66.2, 111.5, 113.8, 120.7, 1277.9, 128.7, 129.3, 130.5, 131.3, 140.4, 152.2, 153.5, 157.3, 190.5; MS: m/z=393.41 [M]$^+$; Analysis: for $C_{22}H_{23}N_3O_4$, calcd. C 67.16, H 5.89, N 10.68%; found C 66.89, H 5.87, N 10.64%.

DHPM-17 4-(4-hydroxyphenyl)-5-[4-(morpholin-4-yl)benzoyl]-3,4-dihydropyrimidin-2(1H)-one Yield: 60%; m.p.: 118-120° C.; $^1H$ NMR (500 MHz, DMSO-$d_6$): δ=9.14 (1H, s, NH, $D_2O$ exchg.), 9.01 (1H, s, OH), 8.08 (1H, s, =CH), 7.43-7.77 (4H, m, Ar—H), 7.07 (1H, s, NH, $D_2O$ exchg.), 6.70-7.05 (4H, m, Ar—H), 5.35 (1H, s, H-4), 3.74 (4H, t, J=4.6 Hz, $2×CH_2$ morpholine), 3.21 (4H, t, J=4.6 Hz, $2×CH_2$ morpholine); $^{13}C$ NMR (125.76 MHz, DMSO-d6): δ=47.0, 53.5, 66.3, 113.4, 115.5, 128.4, 136.5, 132.6, 135.2, 139.3, 152.0, 153.5, 154.5, 154.7, 190.7; MS: m/z=379.41 [M]$^+$; Analysis: for $C_{21}H_{21}N_3O_4$, calcd. C 66.48, H 5.58, N 11.08%; found C 66.72, H 5.60, N 11.04%.

DHPM-18 4-(3-hydroxyphenyl)-5-[4-(morpholin-4-yl)benzoyl]-3,4-dihydropyrimidin-2(1H)-one Yield: 60%; m.p.: 120-122° C.; $^1H$ NMR (500 MHz, DMSO-$d_6$): δ=9.19 (1H, s, NH, $D_2O$ exchg.), 9.01 (1H, s, OH), 8.08 (1H, s, =CH), 7.43-7.77 (4H, m, Ar—H), 7.06 (1H, s, NH, $D_2O$ exchg.), 6.63-7.01 (4H, m, Ar—H), 5.37 (1H, s, H-4), 3.72 (4H, t, J=4.6 Hz, $2×CH_2$ morpholine), 3.20 (4H, t, J=4.6 Hz, $2×CH_2$ morpholine); $^{13}C$ NMR (125.76 MHz, DMSO-$d_6$): δ=48.9, 55.2, 57.8, 66.7, 114.6, 131.2, 138.9, 140.1, 140.8, 147.4, 153.4, 154.6, 154.8, 155.8, 159.2, 192.0; MS: m/z=379.42 [M]$^+$; Analysis: for $C_{21}H_{21}N_3O_4$, calcd. C 66.48, H 5.58, N 11.08%; found C 66.63, H 5.59, N 11.12%.

DHPM-19 4-(3-methoxyhenyl)-5-[4-(morpholin-4-yl)benzoyl]-3,4-dihydropyrimidin-2(1H)-one Yield: 60%; m.p.: 170-172° C.; $^1$H NMR (500 MHz, DMSO-d$_6$): δ=9.23 (1H, d, NH, D$_2$O exchg.), 8.09 (1H, s, =CH), 7.24-7.79 (4H, m, Ar—H), 6.87 (1H, s, NH, D$_2$O exchg.), 6.91-7.04 (4H, m, Ar—H), 5.45 (1H, s, H-4), 3.83 (3H, s, OCH$_3$), 3.73 (4H, t, J=4.6 Hz, 2×CH$_2$ morpholine), 3.22 (4H, t, J=4.6 Hz, 2×CH$_2$ morpholine); $^{13}$C NMR (125.76 MHz, DMSO-d6): δ=47.0, 53.9, 66.2, 112.7, 113.8, 118.9, 128.5, 130.1, 130.5, 139.8, 146.1, 152.0, 153.5, 159.7, 190.7; MS: m/z=393.40 [M]$^+$; Analysis: for C$_{22}$H$_{23}$N$_3$O$_4$, calcd. C 67.16, H 5.89, N 10.68%; found C 66.87, H 5.91, N 10.66%.

DHPM-20 4-(4-ethoxyphenyl)-5-[4-(morpholin-4-yl)benzoyl]-3,4-dihydropyrimidin-2(1H)-one Yield: 60%; m.p.: 200-202° C.; $^1$H NMR (500 MHz, DMSO-d$_6$): δ=9.16 (1H, s, NH, D$_2$O exchg.), 8.08 (1H, s, =CH), 6.86-7.77 (8H, m, Ar—H), 6.78 (1H, s, NH, D$_2$O exchg.), 5.38 (1H, s, H-4), 3.97 (2H, q, J=6.9 Hz, OCH$_2$), 3.73 (4H, t, J=4.6 Hz, 2×CH$_2$ morpholine), 3.21 (4H, t, J=4.6 Hz, 2×CH$_2$ morpholine), 1.27 (3H, t, J=6.9 Hz, CH$_3$); $^{13}$C NMR (125.76 MHz, DMSO-d6): δ=47.6, 53.4, 63.2, 66.3, 113.2, 113.8, 114.2, 114.6, 125.8, 128.0, 129.5, 130.4, 132.7, 136.7, 137.4, 138.8, 139.5, 151.9, 153.3, 154.6, 157.1, 158.2, 190.7, 192.8; MS: m/z=407.42 [M]$^+$; Analysis: for C$_{23}$H$_{25}$N$_3$O$_4$, calcd. C 67.80, H 6.18, N 10.31%; found C 66.88, H 6.20, N 10.35%.

It is to be understood that the dihydropyrimidinone derivatives are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A compound having the chemical structure according to Formula 1:

(Formula 1)

wherein

Z is selected from N and O;

X is selected from O and S; and

R is selected from aryl, substituted aryl, heteroaryl, or substituted heteroaryl;

or a pharmaceutically acceptable salt thereof.

2. The compound according to claim 1, wherein:

R is substituted aryl or substituted heteroaryl, the substituted aryl or substituted heteroaryl having one or more substituents selected from halogen, alkyl, haloalkyl, alkoxy, haloalkoxy, nitro, hydroxyl, alkylthio, alkylamino, heteroaryl, aryloxy, haloaryloxy, arylthio, and arylamino.

3. The compound according to claim 1, wherein the compound is selected from the group consisting of:

(DHPM-1)

(DHPM-2)

(DHPM-3)

(DHPM-4)

(DHPM-5)

-continued (DHPM-6)

(DHPM-7)

(DHPM-8)

(DHPM-9)

(DHPM-10)

4. The compound according to claim 1, wherein Z is oxygen.

5. The compound according to claim 4, wherein the compound is selected from the group consisting of:

(DHPM-11)

(DHPM-12)

(DHPM-13)

(DHPM-14)

(DHPM-15)

-continued

(DHPM-16)

(DHPM-17)

(DHPM-18)

(DHPM-19)

and (DHPM-20)

6. A compound having a chemical structure according to Formula 1:

(Formula 1)

wherein
Z is selected from N and O;
X is selected from O and S; and
R is phenyl, 2-nitrophenyl, 3-nitrophenyl, 4-nitrophenyl, 4-chlorophenyl, 2-methoxyphenyl, 4-hydroxyphenyl, 3-hydroxyphenyl, 3-methoxyphenyl, or 4-ethoxy phenyl;
or a pharmaceutically acceptable salt thereof.

7. The compound according to claim 6, wherein Z is nitrogen.

8. A method of preparing a compound having a chemical structure according to Formula 1:

(Formula 1)

wherein
Z is selected from N and O;
X is selected from O and S; and
R is selected from aryl, substituted aryl, heteroaryl, or substituted heteroaryl;
or a pharmaceutically acceptable salt thereof;
the method comprising
refluxing 1-[4-(piperazin/morpholin-1-yl)phenyl]ethan-1-one with dimethyl-formamide dimethylacetal (DMF-DMA) to produce an enaminone; and
refluxing a solution of the enaminone with a substituted benzaldehyde, urea, and glacial acetic acid to produce the compound.

9. The method of claim 8, wherein the 1-[4-(piperazin/morpholin-1-yl)phenyl]ethan-1-one is refluxed with the dimethylformamide dimethylacetal (DMF-DMA) under a solvent free condition for about 10 hours to produce the enaminone.

10. The method of claim 8, wherein the solution of enaminone, substituted benzaldehyde, urea, and glacial acetic acid is refluxed for about 3 hours to produce the compound.

11. The method of claim 8, further comprising:
recrystallizing the compound from a mixture of ethanol and glacial acetic acid.

12. The method of claim 8, wherein R is phenyl, 2-nitrophenyl, 3-nitrophenyl, 4-nitrophenyl, 4-chlorophenyl, 2-methoxyphenyl, 4-hydroxyphenyl, 3-hydroxyphenyl, 3-methoxyphenyl, or 4-ethoxy phenyl.

13. The method of claim 12, wherein Z is N.
14. The method of claim 12, wherein Z is O.

* * * * *

UNITED STATES PATENT AND TRADEMARK OFFICE
CERTIFICATE OF CORRECTION

PATENT NO. : 10,111,873 B1  
APPLICATION NO. : 15/873450  
DATED : October 30, 2018  
INVENTOR(S) : Mashooq Ahmad Bhat and Mohamed A. Al-Omar Page 1 of 1

It is certified that error appears in the above-identified patent and that said Letters Patent is hereby corrected as shown below:

On the Title Page

At Item (12) delete "Bhat" and insert --Bhat et al.--

At Item (72) Inventor should read:  
Mashooq Ahmad Bhat, Riyadh, (SA)  
Mohamed A. Al-Omar, Riyadh (SA)

Signed and Sealed this  
Fifth Day of February, 2019

Andrei Iancu  
*Director of the United States Patent and Trademark Office*